United States Patent [19]

Hassall et al.

[11] 4,341,781

[45] Jul. 27, 1982

[54] PYRIDAZOPYRIDAZINE DERIVATIVES

[75] Inventors: Cedric H. Hassall, Hatfield; Christopher J. Moody, Stevenage, both of England

[73] Assignee: Hoffmann-La Roche Inc., Nutley, N.J.

[21] Appl. No.: 186,237

[22] Filed: Sep. 11, 1980

[30] Foreign Application Priority Data

Sep. 19, 1979 [GB] United Kingdom ................ 7932531
Jul. 11, 1980 [GB] United Kingdom ................ 8022701

[51] Int. Cl.$^3$ .................... A61K 31/50; C07D 487/04; C07D 237/04
[52] U.S. Cl. .................................... 424/250; 544/224; 544/235
[58] Field of Search ........................ 544/235; 424/250
[56] References Cited

U.S. PATENT DOCUMENTS 2,921,068  1/1960  Clarke et al. .................... 544/235
3,062,820  11/1962 Kealy ................................. 544/235
3,948,908  4/1976  Yurugi et al. ........................ 544/80

FOREIGN PATENT DOCUMENTS 593284  11/1977 Switzerland .

OTHER PUBLICATIONS

Davies et al. J. Chem. Soc. Perkin Trans 1, 1976, pp. 2390-2394.
Chem. Abs. 52, 4698 (1957).
Gubitz et al., Chem. Abs. 55, 16561d (1961).
Kealy et al. 56, 15508f (1962).

*Primary Examiner*—Mark L. Berch
*Attorney, Agent, or Firm*—Jon S. Saxe; Bernard S. Leon; James H. Callwood

[57] ABSTRACT

The present invention relates to pyridazopyridazine derivatives, a process for the preparation thereof, pharmaceutical preparations containing said derivatives and the use of said derivatives as antihypertensive agents.

15 Claims, No Drawings

PYRIDAZOPYRIDAZINE DERIVATIVES

SUMMARY OF THE INVENTION

The pyridazopyridazine derivatives provided by the present invention are compounds of the formula

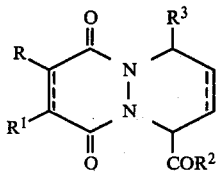

wherein one of the symbols R and $R^1$ is hydrogen or lower alkyl and the other symbol is a group of the formula $$-(A)_n-Y \qquad (i)$$

in which A is methylene, ethylene or propylene which may be substituted by lower alkyl, Y is mercapto, lower alkanoylthio, aroylthio or aryl-(lower alkylthio) and n is zero or 1, $R^2$ is hydroxy, lower alkoxy or amino, $R^3$ is a hydrogen or lower alkyl or aryl and the broken lines denote optional bonds, and salts of the acids of formula I with pharmaceutically acceptable bases.

DETAILED DESCRIPTION OF THE INVENTION

As used in this specification, the term "lower alkyl," alone or in combination, means a straight-chain or branched-chain alkyl group which preferably contains from 1 to 6 carbon atoms, for example, methyl, ethyl, propyl, isopropyl, butyl, tert.butyl, pentyl and hexyl. The term "lower alkoxy" means a straight-chain or branched-chain alkoxy group which preferably contains from 1 to 6 carbon atoms, for example, methoxy, ethoxy, propoxy, isopropoxy butoxy. The lower alkanoyl moiety of a lower alkanoylthio group is derived from a straight-chain or branched-chain alkanoic acid which preferably contains from 2 to 6 carbon atoms such as acetic acid, propionic acid, butyric acid, isobutyric acid, valeric acid, pivalic acid, etc., examples of lower alkanoylthio groups thus being acetylthio, propionylthio, etc. The aroyl moiety of an aroylthio group is derived from an aromatic carboxylic acid such as benzoic acid, etc. The term "aryl," alone or in combination, means the phenyl which may be unsubstituted or optionally substituted with one or more substituants selected from halogen, lower alkyl, lower alkoxy, trifluoromethyl and the like. An example of an aryl-(lower alkylthio) group is the benzylthio group. The term "halogen" means fluorine, chlorine, bromine or iodine.

A preferred class of compounds of formula I comprises those in which R is hydrogen, $R^1$ is a group of formula (i) hereinbefore, $R^2$ is hydroxy or lower alkoxy, $R^3$ is hydrogen and a single-bond is present in the 7,8- position. As regards the group of formula (i), this preferably represents a mercaptomethyl group or a lower alkanoylthiomethyl group such as the acetylthiomethyl group.

Particularly preferred compounds of formula I hereinbefore are:
racemic methyl 8-(acethylthio)methyl-octahydro-6,9-dioxopyridazo[1,2-a]pyridazine-1-carboxylate and
racemic 8-(mercaptomethyl)-octahydro-6,9-dioxopyridazo-[1,2-a]pyridazine-1-carboxylic acid.

Further examples of preferred compounds of formula I hereinbefore are:
racemic tert.butyl 8-(acetylthio)methyl-octahydro-6,9-dioxopyridazo[1,2-a]pyridazine-1-carboxylate,
racemic 8-(acetylthio)methyl-octahydro-6,9-dioxopyridazo[1,2-a]pyridazine-1-carboxylic acid,
racemic methyl 8-(acetylthio)methyl-1,4,6,7,8,9-hexahydro-6,9-dioxopyridazo[1,2-a]pyridazine-1-carboxylate,
racemic 8-(mercaptomethyl)-1,4,6,7,8,9-hexahydro-6,9-dioxopyridazo[1,2-a]pyridazine-1-carboxylic acid,
(+)-methyl 8-(acetylthio)methyl-1,4,6,7,8,9-hexahydro-6,9-dioxopyridazo[1,2-a]pyridazine-1-carboxylate,
(−)-methyl 8-(acetylthio)methyl-1,4,6,7,8,9-hexahydro-6,9-dioxopyridazo[1,2-a]pyridazine-1-carboxylate
and
(−)-8-(mercaptomethyl)-1,4,6,7,8,9-hexahydro-6,9-dioxopyridazo[1,2-a]pyridazine-1-carboxylic acid.

According to the process provided by the present invention, the pyridazopyridazine derivatives aforesaid, that is the compounds of formula I hereinbefore and salts of the acids of formula I with pharmaceutically acceptable bases are prepared by (a) for the preparation of a compound of formula I in which $R^2$ is lower alkoxy, $R^3$ is hydrogen and single-bonds are present in the 2,3- and 7,8-positions, cyclizing a compound of the formula

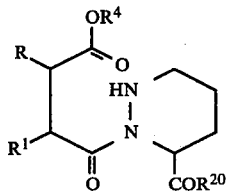

wherein R and $R^1$ are as above, $R^4$ is hydrogen or lower alkyl and $R^{20}$ is lower alkoxy, or (b) for the preparation of a compound of formula I in which $R^2$ is hydroxy, $R^3$ is hydrogen and a single-bond is present in the 2,3-position, reacting the compound of the formula

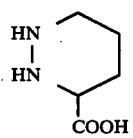

with an anhydride of the formula

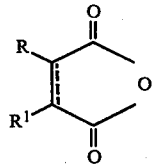

wherein R, $R^1$ and the broken line are as above, or (c) for the preparation of a compound of formula I in which a double-bond is present in the 2,3-position, reacting a compound of the formula

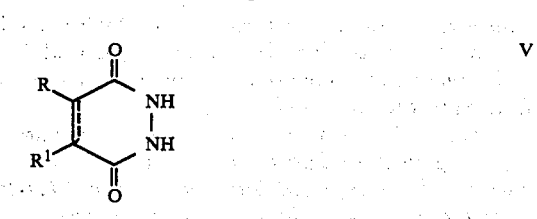

wherein R, R$^1$ and the broken line are as above, under oxidizing conditions with a compound of the formula

wherein R$^2$ and R$^3$ are as above or (d) for the preparation of a compound of formula I, in which R$^2$ is hydroxy and a double-bond is present in the 2,3-position, oxidizing a compound of the formula

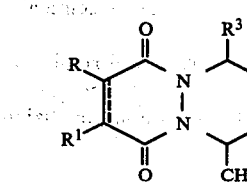

wherein R, R$^1$, R$^3$ and the broken lines are as above, or (e) for the preparation of a compound of formula I in which Y in the group of formula (i) is lower alkanoylthio, aroylthio or aryl-(lower alkylthio), reacting a compound of the formula

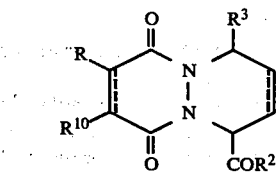

wherein R$^2$ and R$^3$ and the broken lines are as above and one of the symbols R and R$^{10}$ is hydrogen or lower alkyl and the other symbol is a group of the formula $$-(A)_n-X \qquad \text{(ii)}$$

in which A and n are as above and X is halogen, with a compound of the formula $$R^6-SH \qquad \text{VIII}$$

wherein R$^6$ is lower alkanoyl, aroyl or aryl-(lower alkyl), or (f) for the preparation of a compound of formula I in which Y in the group of formula (i) is mercapto, cleaving off the lower alkanoyl, aroyl or aryl-(lower alkyl) group from a corresponding compound of formula I in which Y is lower alkanoylthio, aroylthio or aryl-(lower alkylthio), or (g) for the preparation of a compound of formula I in which R is hydrogen, R$^1$ is a group of formula (i) in which A is methylene, Y is lower alkanoylthio or aroylthio and n is 1, R$^2$ is lower alkoxy, R$^3$ is hydrogen and single-bonds are present in the 2,3-and 7,8-positions, cyclizing a compound of the formula

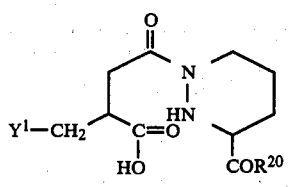

wherein R$^{20}$ is as above and Y$^1$ is lower alkanoylthio or aroylthio, or (h) for the preparation of a compound of formula I in which R is hydrogen, R$^1$ is a group of formula (i) in which A is methylene, Y is lower alkanoylthio or aroylthio and n is 1, R$^2$ is hydroxy or lower alkoxy and a single-bond is present in the 7,8-position, reacting a compound of the formula

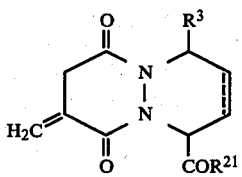

wherein R$^3$ and the broken line are as above and R$^{21}$ is hydroxy or lower alkoxy, with a compound of formula VIII in which R$^6$ is lower alkanoyl or aroyl, or (i) for the preparation of a compound of formula I in which R$^2$ is lower alkoxy or amino, esterifying or amidating a corresponding compound of formula I in which R$^2$ is hydroxy, or (j) for the preparation of a compound of formula I in which R$^2$ is hydroxy, treating a corresponding compound of formula I in which R$^2$ is lower alkoxy with an acid or a base, or (k) if desired, separating a diastereoisomer mixture obtained into the diastereoisomer racemates, and/or (l) if desired, resolving a racemate obtained into the two antipodes, and/or (m) if desired, converting an acid of formula I into a salt with a pharmaceutically acceptable base.

The method by which the cyclization of a compound of formula II is carried out in accordance with embodiment (a) of the process depends upon the nature of R$^4$. When R$^4$ is hydrogen, the cyclization comprises a dehydration, and this can be carried out in a known manner, for example, using phosphorus pentachloride in the presence of an inert organic solvent such as dimethylformamide at a low temperature, for example, about 0° followed by treatment with a tertiary organic base such as pyridine at about room temperature. On the other hand, when R$^4$ in the compound of formula II is lower alkyl, the cyclization comprises removing the elements of the corresponding lower alkanol R$^4$—OH from said compounds. This cyclization method can likewise be carried out in a known manner, for example, by heating in the presence of a suitable organic acid such as acetic acid.

The compounds of formula II in which R$^4$ is hydrogen are preferably used in the process in situ, that is to say, without isolation from the medium in which they are prepared.

The reaction of the compound of formula III, that is piperazic acid, with an anhydride of the formula IV in accordance with embodiment (b) of the process can be carried out, for example, by heating the reactants together in the presence of an acid. In a preferred embodiment, dilute hydrochloric acid is used as the acid, and the heating is carried out at the reflux temperature of the reaction mixture.

The reaction of a compound of formula V with a compound of formula VIa in accordance with embodiment (c) of the process is carried out under oxidizing conditions which can suitably be provided by including an oxidizing agent such as lead tetraacetate, tert.butyl hypochlorite or the like in the reaction mixture. The reaction is suitably carried out in the presence of an inert organic solvent, examples of such solvents being aromatic hydrocarbons, for example, benzene, toluene etc., halogenated hydrocarbons, for example, dichloromethane, chloroform, chlorobenzene, etc., di(lower alkyl) ketones, for example, acetone, methyl ethyl ketone, etc., ethers, for example, diethyl ether, dioxane, tetrahydrofuran, etc., acetonitrile, ethyl acetate, etc. The reaction can be carried out at a temperature between about $-80°$ C. and the boiling point of the reaction mixture, preferably at about room temperature.

The oxidation of a compound of formula XVIII in accordance with embodiment (d) of the process is carried out in a known manner under oxidizing conditions which are suitably used for the oxidation of alcohols to the corresponding carboxylic acid, for example, using a chromic oxidizing agent.

The reaction of a compound of formula VII with a compound of formula VIII in accordance with embodiment (e) of the process is preferably carried out in the presence of a base and in an inert solvent. Included among the bases which can be used are alkali metal hydroxides, for example, sodium hydroxide and potassium hydroxide, alkali metal hydrides, for example, sodium hydride and potassium hydride, alkali metal lower alkoxides, for example, sodium methoxide, sodium ethoxide, etc., and alkali metal carbonates, for example, sodium carbonate and potassium carbonate. When $R^6$ in the compound of formula VIII is lower alkanoyl or aroyl, suitable solvents are di (lower alkyl) ketones, for example, acetone and dimethylformamide or, when an alkali metal carbonate is used as the base, a mixture of water and a chlorinated hydrocarbon, for example, methylene chloride or a mixture of water and ethyl acetate. When $R^6$ in the compound of formula VIII is aryl-(lower alkyl), suitable solvents are water, dimethylformamide, etc. It may be expedient to use a compound of formula VIII in which $R^6$ is lower alkanoyl or aroyl in the form of an alkali metal salt, for example, the potassium salt, and to carry out the reaction in the presence of a catalytic amount of an alkali metal iodide, for example, potassium iodide. The reaction of a compound of formula VII with a compound of formula VIII can be carried out at a temperature of from about 10° C. to reflux temperature of the reaction mixture. It is preferred to carry out the reaction at the reflux temperature of the reaction mixture.

The cleavage in accordance with embodiment (f) of the process can be carried out in a known manner. The particular cleavage method depends on the nature of the group to be cleaved off. For example, when a lower alkanoyl or aroyl group is to be cleaved off, the cleavage can be carried out using an aqueous alkali metal hydroxide, for example, aqueous sodium hydroxide or aqueous potassium hydroxide, aqueous ammonia or a lower alkanol, for example, methanol, in the presence of the corresponding alkali metal lower alkoxide, for example, sodium methoxide. The use of aqueous ammonia is preferred. Again, for example, when an aryl-(lower alkyl) group is to be cleaved off, the cleavage can be carried out using sodium in liquid ammonia.

The cyclization of a compound of formula IX in accordance with embodiment (g) of the process comprises a dehydration which can be carried out in a known manner, for example, using phorphorus pentachloride in the presence of an inert organic solvent such as tetrahydrofuran at a temperature of from about 0° C. to about room temperature. The compounds of formula IX are preferably cyclized in situ.

In accordance with embodiment (h) of the process, a compound of formula X is reacted with a compound of formula VIII in which $R^6$ is lower alkanoyl or aroyl. This reaction can be carried out readily by allowing a mixture of a compound of formula X and a compound of formula VIII to stand at about room temperature.

The esterification or amidation of a compound of formula I in which $R^2$ is hydroxy to give a compound of formula I in which $R^2$ is lower alkoxy or amino in accordance with embodiment (i) of the process can be carried out in a known manner. For example, the esterification can be carried out by reacting a compound of formula I in which $R^2$ is hydroxy with a lower alkanol, for example, methanol, ethanol, etc., in the presence of an appropriate acid, for example, a mineral acid such as hydrochloric acid or with a suitable diazoalkane, for example, diazomethane. Alternatively, a compound of formula I in which $R^2$ is hydroxy can firstly be converted in a known manner by treatment with a chlorinating agent such as thionyl chloride, phosphorus trichloride or phosphorus pentachloride into a corresponding acid chloride which is then reacted, likewise in a known manner with a lower alkanol. A tert.butyl ester can also be obtained by reacting a compound of formula I in which $R^2$ is hydroxy with isobutene in the presence of sulfuric acid. An amide can be obtained, for example, by treating an aforementioned acid chloride with ammonia in a conventional manner.

In accordance with embodiment (j) of the process, a compound of formula I in which $R^2$ is lower alkoxy is converted into a compound of formula I in which $R^2$ is hydroxy. This embodiment can be carried out in a known manner, for example, by treatment with an alkali metal hydroxide such as sodium hydroxide or potassium hydroxide, conveniently at a temperature between room temperature and the boiling point of the mixture, or, where the lower alkoxy group $R^2$ is the tert.butoxy group, by treatment with anhydrous acid.

The compound of formula I contains an asymmetric center at the 1-position and can, therefore, exist in racemic or optically active form. Compounds of formula I which contain more than one asymmetric center can exist in various diastereoisomeric forms. It will be appreciated that this invention includes within its scope all possible stereoisomers of the compounds of formula I and all possible diastereoisomer mixtures and racemates, as well as the separation of diastereoisomer mixtures and the cleavage of racemates which can be carried out according to known methods.

Acids of formula I can be converted into salts with pharmaceutically acceptable bases in accordance with embodiment (m) of the present process. Thus, for example, acids of formula I can be converted into salts by treatment with alkali metal hydroxides, for example, sodium hydroxide and potassium hydroxide, alkaline earth metal hydroxide, for example, calcium hydroxide and magnesium hydroxide, organic bases, for example dicyclohexylamine, etc., basic amino acids, for example, lysine and arginine, etc.

The starting materials of formula II hereinbefore can be prepared, for example, by converting N-benzyloxycarbonylpiperazic acid of the formula

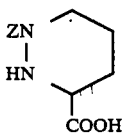   XI wherein Z is benzyloxycarbonyl, into a lower alkyl ester thereof of the formula

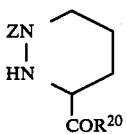   XII wherein $R^{20}$ and Z are as above, reacting this lower alkyl ester with an acid chloride of the formula

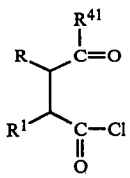   XIII wherein R and $R^1$ are as above and $R^{41}$ is lower alkoxy or benzyloxy, and cleaving off the benzyloxycarbonyl group denoted by Z in the resulting compound of the formula

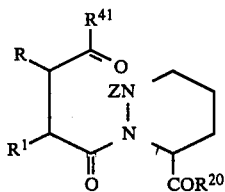   XIV wherein R and $R^1$ are as above.

The conversion of N-benzoyloxycarbonylpiperazic acid of formula XI into a lower alkyl ester of formula XII can be carried out in a known manner for the conversion of carboxylic acids into carboxylic acid esters. Preferably, N-benzyloxycarbonylpiperazic acid is converted into the methyl ester using diazomethane.

The reaction of a lower alkyl ester of formula XII with an acid of formula XIII can be carried out under the conditions of a Schotten-Baumann reaction. Thus, for example, a lower alkyl ester, preferably the methyl ester, of formula XII can be reacted with an acid chloride of formula XIII in an inert organic solvent, for example, a halogenated hydrocarbon such as dichloromethane, in the presence of dilute sodium hydroxide at about room temperature.

The cleavage of the benzyloxycarbonyl group denoted by Z in a compound of formula XIV is carried out in a known manner, for example, by treatment with hydrogen bromide in glacial acetic acid at about room temperature. A benzyloxy group denoted by $R^{41}$ is converted into a hydroxy group during this hydrolysis.

The acid chlorides of formula XIII, insofar as they are not known, can be prepared, for example, in the manner described in the following Examples or in analogy thereto.

The starting materials of formulas III, IV, VIa and VIII hereinbefore and VIb hereinbelow are either known or can be prepared in analogy to the known compounds.

The starting materials of formula V hereinbefore can be prepared, for example, by reacting a compound of formula IV hereinbefore with hydrazine.

The starting materials of formula XVIII hereinbefore can be prepared, for example, in a manner analogous to that described earlier in connection with embodiment (c) of the process using a compound of formula V hereinbefore and a compound of the formula

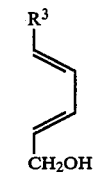   VIb wherein $R^3$ is as above.

The starting materials of formula VII hereinbefore can be prepared, for example, in a manner analogous to that described earlier in connection with embodiments (a), (b) and (c) of the process using starting materials corresponding to formulas II, IV, and V, respectively, but in which the group of formula (i) therein is replaced by a group of formula (ii) hereinbefore. A thus-prepared compound of formula VII in which a double-bond is present in the 2,3-position can, if desired, be catalytically hydrogenated to give a corresponding compound of formula VII in which a single-bond is present in the 2,3-position. Suitable catalysts which may be used are noble metal catalysts such as, for example, palladium, platinum, ruthenium, rhodium and Raney-nickel. The catalyst may be supported on a suitable carrier material, for example, palladium-on-carbon, rhodium-on-alumina, etc. The catalytic hydrogenation can be carried out in a conventional inert organic solvent such as, for example, an aromatic hydrocarbon, for example, benzene, toluene, xylene, etc., a lower alkanol, for example, methanol, ethanol, etc., or an ether, for example, dioxane, etc. The catalytic hydrogenation is advantageously carried out at room temperature and at atmospheric pressure.

The starting materials of formula IX hereinbefore can be prepared, for example, by cleaving of the benzyloxycarbonyl group from a lower alkyl ester of formula XII hereinbefore, reacting the resulting compound of the formula

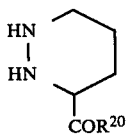

wherein $R^{20}$ is as above, with itaconic anhydride and reacting the resulting compound of the formula

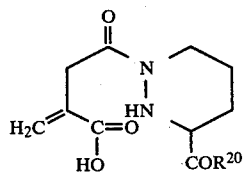

wherein $R^{20}$ is as above, with a compound of formula VIII hereinbefore in which $R^6$ is lower alkanoyl or aroyl.

The cleavage of the benzyloxycarbonyl group from a lower alkyl ester of formula XII can be carried out in a known manner, for example, using hydrogen in the presence of a catalyst such as palladium-on-carbon.

The reaction of a compound of formula XV with itaconic anhydride is suitably carried out in an inert organic solvent, for example, an ether such as dioxane, and at a temperature of about room temperature.

The reaction of a compound of formula XVI with a compound of formula VIII in which $R^6$ is lower alkanoyl or aroyl be carried out in a manner analogous to that described earlier in connection with embodiment (h) of the process provided by the invention.

The starting materials of formula X hereinbefore can be prepared, for example, by reacting a compound of the formula

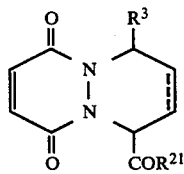

wherein $R^3$, $R^{21}$ and the broken line are as above, with a triaryl phosphine and treating the reaction product obtained with formaldehyde.

The reaction of a compound of formula XVII with a triaryl phosphine, preferably triphenyl phosphine, can be carried out in a known manner. For example, the reaction can be carried out at about room temperature in the presence of a suitable acid such as acetic acid.

The treatment of the reaction product with formaldehyde is conveniently carried out using a solution of formaldehyde in water containing a small amount of methanol. Advantageously, this treatment is carried out at about room temperature.

Those compounds of formula XVII in which a double-bond is present in the 2,3-position can be prepared, for example, by reacting 3,6-dioxo-1,2,3,6-tetrahydropyridazine or, preferably, an alkali metal salt thereof such as the potassium salt, under oxidizing conditions with a compound of formula VIa or VIb hereinbefore and, where a product which contains a hydroxymethyl group in the 1-position is obtained, converting said carboxy group in a known manner.

The aforementioned reaction of 3,6-dioxo-1,2,3,6-tetrahydropyridazine or an alkali metal salt thereof with a compound of formula VIa or VIb and the subsequent conversion of a hydroxymethyl group which may be present in the reaction product into a carboxy group can be carried out in essentially the same manner as that described earlier in connection with embodiments (c) and (d) of the process provided by the present invention.

The compounds of formula XVII hereinbefore in which a singel-bond is present in the 2,3-position can be prepared, for example, by catalytically hyrogenating a corresponding compound of formula XVII in which a double-bond is present in the 2,3-position in an analogous manner to that described earlier in connection with the catalytic hydrogenation of a compound of formula VII in which a double-bond is present in the 2,3-position.

The compound of formula XVII hereinbefore in which $R^{21}$ is hydroxy and $R^3$ is hydrogen can also be prepared, for example, by reacting piperazic acid of formula III hereinbefore with maleic anhydride. This reaction can be carried out in essentially the same manner as that described earlier in connection with embodiment (b) of the process provided by the present invention.

Compounds of formula XVII in which $R^{21}$ is lower alkoxy can be converted into corresponding compounds of formula XVII in which $R^{21}$ is hydroxy in a manner analogous to that described earlier in connection with embodiment (j) of the process provided by the present invention.

Furthermore, compounds of formula XVII in which $R^{21}$ is hydroxy can be esterified in a manner analogous to that described in connection with embodiment (i) of the process provided by the present invention to give a corresponding compound of formula XVII in which $R^{21}$ is lower alkoxy.

The compounds of formulas II, VII, IX, X, XVII and XVIII hereinbefore also form part of the present invention. In addition to being useful intermediates in the process provided by the present invention, compounds of formula XVII in which $R^{21}$ is hydroxy have a pharmacological activity similar to that described hereinafter in relation to the pyridazopyridazine derivatives provided by the invention and can be used as medicaments in the same manner and in the same dosages as described hereinafter in connection with said pyridazopyridazine derivatives.

The pyridazopyridazine derivatives provided by the present invention are useful as antihypertensive agents. They inhibit angiotensin converting enzyme (ACE) which brings about the conversion of angiotensin I into angiotensin II and are, therefore, useful in reducing or alleviating angiotensin-related hypertension.

The activity of the present pyridazopyridazine derivatives in inhibiting angiotensin converting enzyme in vitro can be determined by the following test.

The method used is based on the method of Cushman and Cheung (Biochem. Pharmacol., 20, 1637–1648) incorporating the modifications introduced by Hayakari, et al. (Anal. Biochem., 84, 361–369). The substrate (hippuryl-histidyl-leucine, 2 mM) is incubated with angiotensin converting enzyme in the presence or absence of various concentrations of test substance in potassium phosphate buffer (pH 8.3; 100 mM) containing sodium chloride (300 mM) for 25 minutes at 37° C. (total value 500 μl). The reaction is terminated by the addition of 3 ml of potassium phosphate buffer (pH 8.3; 200 mM) at 0° C. 2,4,6-Trichloro-s-triazine (3%) in 1.5 ml of dioxane is added and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophotometrically at 382 nm. $IC_{50}$ values are defined as the concentration of test substance which reduces by 50% the cleavage of hippuryl-histidylleucine by angiotensin converting enzyme under the aforementioned conditions.

In the foregoing test, racemic 8-(mercaptomethyl)-octahydro-6,9-dioxopyridazo[1,2-a]pyridazine-1-carboxylic acid exhibits an $IC_{50}$ (M) of $6.25 \times 10^{-8}$.

The pyridazopyridazine derivatives provided by the present invention can be used as medicaments in the form of pharmaceutical preparations which contain them in association with a compatible pharmaceutical carrier material. The carrier material can be organic or inorganic carrier material which is suitable for enteral, for example, oral, or parenteral administration, examples of such carrier materials being water, gelatin, gum arabic, lactose, starch, magnesium stearate, talc, vegetable oils, polyalkyleneglycols, petroleum jelly, etc. The pharmaceutical preparations can be made up in a solid form, for example, as tablets, dragees, suppositories or capsules or in a liquid form, for example, as solutions, suspensions or emulsions. The pharmaceutical preparations may be subjected to standard pharmaceutical operations such as sterilization and/or may contain adjuvants such as preserving, stabilizing, wetting or emulsifying agents, salts for varying the osmotic pressure or buffers. The pharmaceutical preparations may also contain other thereapeutically valuable substances.

The pyridazopyridazine derivatives provided by the present invention maybe administered to adults in a daily dosage of from about 0.1 mg to 100 mg, preferably about 1 mg to 50 mg, per kilogram body weight. The daily dosage may be administered as a single dose or in divided doses. It will be appreciated that the aforementioned dosage range is given by way of example only and can be varied upwards or downwards depending on factors such as the severity of the indication being treated and the condition of the patient as determined by the attending physician.

The following Examples illustrate the process provided by the present invention:

EXAMPLE 1

(A) 18.0 g (0.068 mol) of racemic 1-benzyloxycarbonylpiperazic acid were suspended in 450 ml of dry diethyl ether and the suspension was treated with a solution of diazomethane in diethyl ether (ca 0.1 mol). The mixture was stirred at room temperature for 2 hours, washed with three 10 ml portions of 10% sodium carbonate solution and 100 ml of water, dried over magnesium sulfate and evaporated to give 18.15 g (96%) of racemic 1-benzyloxycarbonylpiperazic acid methyl ester in the form of a brownish oil.

(B) 56 g (0.5 mol) of itaconic anhydride and 54 g (0.5 mol) of benzyl alcohol were heated together on a steambath for 2 hours. The mixture crystallized on cooling. The product was recrystallized from toluene/petroleum ether to give 74.22 g (67%) of monobenzyl itaconate of melting point 77°–82° C.

20 g (0.01 mol) of monobenzyl itaconate and 9.5 ml (0.13 mol) of thioacetic acid were heated under reflux for 3 hours. The excess thioacetic acid was removed by evaporation to give 1-benzyl-3-(acetylthiomethyl)-hydrogen succinate.

The foregoing acid was dissolved in dry diethyl ether, cooled in ice and treated with phosphorus pentachloride to give the corresponding acid chloride.

(C) 15.99 g (0.0575 mol) of racemic 1-benzyloxycarbonylpiperazic acid methyl ester [prepared as described in paragraph (A)] were dissolved in 350 ml of dichloromethane and the solution was stirred rapidly at room temperature. Simultaneously, from separate dropping funnels, there were added dropwise over a period of 15 minutes a solution of the acid chloride [prepared as described in paragraph (B)] in 130 ml of dichloromethane and 0.5 M sodium hydroxide solution (137 ml; 0.068 mol). After completion of the addition, the mixture was stirred at room temperature for 18 hours. The layers were then separated. The organic layer was washed with 200 ml of saturated sodium bicarbonate solution, dried over magnesium sulfate and evaporated to give 31.34 g of a brown oil. This oil was chromatographed on silica gel using diethyl ether/hexane (4:1) as the eluent, there being obtained both diastereoisomers of racemic 1-benzyl-3-methyl-2-[2-(acetylthio)methyl]-3-(benzyloxycarbonyl)propionyl-hexahydro-1,3-pyridazine-dicarboxylate. Diastereoisomer A exhibits $R_f$ 0.6 and diastereoisomer B exhibits $R_f$ 0.5. The total yield is 20.21 g (63%).

(D) 11.16 g (0.02 mol) of diastereoisomer A were dissolved in 25 ml of glacial acetic acid. The solution was treated with 76 ml of 45% hydrogen bromide in acetic acid and the resulting mixture was left to stand at room temperature for 1.25 hours. The mixture was then evaporated and the residue was dissolved in 125 ml of dimethylformamide and cooled to 0° C. 4.47 g (0.021 mol) of phosphorus pentachloride were added and the mixture was stirred at 0° C. for 30 minutes and at room temperature for 2 hours. 23 ml of pyridine were added and the mixture was stirred for a further 2 hours. The solution was evaporated, the residue was dissolved in 600 ml of ethyl acetate and the solution was washed successively with 110 ml of 2 M hydrochloric acid, 200 ml of saturated sodium bicarbonate solution and 150 ml of saturated sodium chloride solution. The organic layer was dried over magnesium sulphate and evaporated to give 7.36 g of a brown oil. Column chromatography on silica gel using chloroform/ethyl acetate (1:1) as the eluent gave 1.15 g (18%) of racemic methyl 8-(acethylthio)methyl-octahydro-6,9-dioxopyridazo[1,2-a]pyridazine-1-carboxylate (diastereoisomer A) of melting point 84°–86° C. (from ethyl acetate/hexane).

In a similar manner, from diastereoisomer B [prepared as described in paragraph (C)] there was obtained in 16% yield racemic methyl 8-(acetylthio)methyl-octahydro-6,9-dioxopyridazo[1,2-a]pyridazine-1-carboxylate (diastereoisomer B) of melting point 130°–132° C. (from ethyl acetate/hexane).

EXAMPLE 2

0.84 (2.67 mmol) of racemic methyl-8-(acetylthio)-methyl-octahydro-6,9-dioxopyridazo[1,2-a]pyridazine-1-carboxylate [diastereoisomer A; see Example 1, paragraph (D)] was dissolved in a mixture of 5 ml of methanol and 10 ml of 1 M sodium hydroxide. The solution was stirred at room temperature under nitrogen for 2 hours, diluted with water and extracted with chloroform. The aqueous layer was acidified with concentrated hydrochloric acid, saturated with sodium chloride and extracted with chloroform. The chloroform extracts were combined, dried over magnesium sulfate and evaporated to give 0.74 g of a colorless solid. This solid was recrystallized from ethyl acetate/hexane, there being obtained 0.36 g (52%) of racemic 8-(mercaptomethyl)-octahydro-6,9-dioxopyridazo[1,2-a]pyridazine-1-carboxylic acid (diastereoisomer A) of melting point 195°–196° C.

EXAMPLE 3

(A) 3.2 g of racemic 1-benzyloxycarbonylpiperazic acid tert.butyl ester were dissolved in 30 ml of methanol and the solution was hydrogenated over 320 mg of 5% palladium-on-carbon. The catalyst was removed by filtration and the filtrate was evaporated to dryness. The resulting crude racemic piperazic acid tert.butyl ester was taken up in 30 ml of dioxane, cooled to 0° C. and treated with a solution of 1.12 g of itaconic anhydride in 10 ml of dioxane. After stirring at room temperature for 4 hours, the solvent was removed and the residue was partitioned between chloroform and saturated sodium bicarbonate solution. The aqueous layer was acidified to pH 2 with hydrochloric acid and extracted with chloroform. The chloroform extracts were dried over magnesium sulfate and evaporated. The residue was crystallized from ethyl acetate to give 1.73 g (57%) of racemic 3-tert.butoxycarbonyl-hexahydro-α-methylene-γ-oxo-1-pyridazinebutyric acid in the form of white crystals of melting point 153°–154° C.

(B) 5.5 g of racemic 3-tert.butoxycarbonyl-hexahydro-α-methylene-γ-oxo-1-pyridazinebutyric acid were stirred in 18 ml of thioacetic acid at room temperature for 3 days. The excess thioacetic acid was removed in vacuo and the residue was taken up in 220 ml of tetrahydrofuran and cooled to 0° C. 3.85 g of phosphorus pentachloride were added and the mixture was stirred at 0° C. for 0.5 hour and at room temperature for 3 hours. The solvent was removed by evaporation and the residue was partitioned between chloroform and saturated sodium bicarbonate solution. The chloroform layer was washed with brine, dried over magnesium sulphate and evaporated. The residue was chromatographed on silica gel using chloroform/ethyl acetate (3:1) for the elution to give 4.05 g (62%) of racemic tert.butyl 8-(acetylthio)methyl-octahydro-6,9-dioxopyridazo[1,2-a]pyridazine-1-carboxylate in the form of an oily mixture of diastereoisomers. Crystallization from ethyl acetate/hexane gave diastereoisomer B in the form of a white solid of melting point 124°–128° C. The mother liquor was evaporated to give mainly diastereoisomer A in the form of an oil.

(C) (i) 2.47 g of crude racemic tert.butyl 8-(acetylthio)methyl-octahydro-6,9-dioxopyridazo[1,2-a]pyridazine-1-carboxylate (diastereoisomer A) were stirred with 25 ml of freshly distilled trifluoroacetic acid at room temperature for 1.5 hours. The solvent was removed by evaporation. The residual solid was re-evaporated with toluene and recrystallized from ethyl acetate/petroleum ether (60°–80° C.) to give 1.57 g (75%) of racemic 8-(acetylthio)methyl-octahydro-6,9-dioxopyridazo[1,2-a]pyridazine-1-carboxylic acid (diastereoisomer A) in the form of a white solid of melting point 148°–149° C.

(C) (ii) In a manner analogous to that described in paragraph (C) (i) of this Example, from 1.29 g of racemic tert.butyl 8-(acetylthio)methyl-octahydro-6,9-dioxopyridazo[1,2-a]pyridazine-1-carboxylate (diastereoisomer B) there was obtained 0.75 g (69%) of racemic 8-(acetylthio)methyl-octahydro-6,9-dioxopyridazo[1,2-a]pyridazine-1-carboxylic acid (diastereoisomer B) in the form of a white solid of melting point 206°–207° C.

(D) (i) 0.08 g of racemic 8-(acetylthio)methyl-octahydro-6,9-dioxopyridazo[1,2-a]pyridazine-1-carboxylic acid (diastereoisomer A) was stirred at room temperature under a nitrogen atmosphere with a mixture of 1 ml of water and 1 ml of 880 ammonium hydroxide for 1 hour. After acidification to pH 1, the solution was saturated with sodium chloride and extracted with chloroform. The chloroform extracts were dried over magnesium sulphate and evaporated. The residue was crystallized from ethyl acetate/hexane to give 0.05 g (73%) of racemic 8-mercaptomethyl-octahydro-6,9-dioxopyridazo[1,2-a]pyridazine-1-carboxylic acid (diastereoisomer A) in the form of a white solid of melting point 194°–196° C.

(D) (ii) In a manner analogous to that described in paragraph (D) (i) of this Example, from racemic 8-(acetylthio)methyl-octahydro-6,9-dioxopyridazo[1,2-a]pyridazine-1-carboxylic acid (diastereoisomer B) there was obtained racemic 8-(mercaptomethyl)-octahydro-6,9-dioxopyridazo[1,2-a]pyridazine-1-carboxylic acid (diastereoisomer B) in the form of a white solid of melting point 162°–166° C.

EXAMPLE 4

(A) 163 g of the potassium salt of 3,6-dioxo-1,2,3,6-tetrahydropyridazine and 122 g of methyl penta-2,4-dienoate were stirred at −15° C. with 2.7 liters of acetonitrile under nitrogen. 130 ml of tert.butyl hypochlorite were added over a period of 35 minutes. The resulting yellow suspension was stirred at −15° C. for 2 hours and then at room temperature overnight. The brown solid was filtered off, washed with 200 ml of acetonitrile and the filtrate and washings were combined and evaporated. The residue was partitioned between dichloromethane and water. The organic layer was dried over magnesium sulphate and evaporated. The residue was washed by decantation with hexane and recrystallized from ethyl acetate to give 84.1 g (35%) of racemic methyl 1,4,6,9-tetrahydro-6,9-dioxopyridazo[1,2-a]pyridazine-1-carboxylate in the form of a pale yellow solid of melting point 143°–145° C.

(B) 6 g of racemic methyl 1,4,6,9-tetrahydro-6,9-dioxopyridazo[1,2-a]pyridazine-1-carboxylate were dissolved in 70 ml of acetic acid and the solution was treated with 7.8 g of triphenylphosphine. The resulting solution was stirred at room temperature for 2 hours and then evaporated to dryness. The residue was treated with 11 ml of 40% formalin solution and the mixture was stirred at room temperature for 3 hours. After evaporation to dryness, the residue was dissolved in 70 ml of thioacetic acid and left to stand at room temperature for 3 days. After evaporation, the residue was chromatographed to give 1.12 g (13%) of racemic methyl 8-(acethylthio)methyl-1,4,6,7,8,9-hexahydro-6,9-dioxopyridazo[1,2-a]pyridazine-1-carboxylate in the form of a white solid of melting point 135°–136° C. (from ethyl acetate/hexane).

EXAMPLE 5

(A) 76.7 g of racemic methyl 1,4,6,9-tetrahydro-6,9-dioxopyridazo[1,2-a]pyridazine-1-carboxylate were boiled under reflux with 350 ml of 2 N hydrochloric acid for 0.75 hour. The mixture was cooled to 0° C. and filtered. The residue was recrystallized from water to give 55.15 g (71%) of racemic 1,4,6,9-tetrahydro-6,9-dioxopyridazo[1,2-a]pyridazine-1-carboxylic acid monohydrate in the form of a white solid of melting point 185°–187° C. (decomposition).

(B) 6.24 g of racemic 1,4,6,9-tetrahydro-6,9-dioxopyridazo[1,2-a]pyridazine-1-carboxylic acid and 8.64 g of triphenylphosphine were warmed for a brief period with 150 ml of acetic acid. The solution was stirred at room temperature for 2.5 hours and then evaporated. The residue was treated at room temperature for 3.5 hours with 11 ml of 40% formalin solution and the mixture was evaporated. The residue was dissolved in 80 ml of thioacetic acid and the solution was left to stand at room temperature for 3 days. After evaporation, the residue was partitioned between chloroform and saturated sodium bicarbonate solution. The aqueous layer was acidified with dilute hydrochloric acid and extracted with chloroform. The chloroform extracts were dried over magnesium sulphate and evaporated, the residual oil being suspended in dioxan. Ethereal diazomethane solution was added to give a permanent yellow color and the excess diazomethane was destroyed with acetic acid. The solvents were removed by evaporation and the residue was taken up in ethyl acetate, washed successively with saturated sodium bicarbonate solution and brine, dried over magnesium sulphate and evaporated. The resulting oil was chromatographed on silica gel to give 1.95 g (23%) of racemic methyl 8-(acetylthio)methyl-1,4,6,7,8,9-hexahydro-6,9-dioxopyridazo[1,2-a]pyridazine-1-carboxylate of melting point 132°–133° C. (from ethyl acetate/hexane).

(C) In a manner analogous to that described in Example 2, from 0.94 g of racemic methyl 8-(acetylthio)methyl-1,4,6,7,8,9-hexahydro-6,9-dioxopyridazo[1,2-a]pyridazine-1-carboxylate there was obtained 0.32 g (41%) of racemic 8-(mercaptomethyl)-1,4,6,7,8,9-hexahydro-6,9-dioxopyridazo[1,2-a]pyridazine-1-carboxylic acid of melting point 155°–162° C. (decomposition) after recrystallization from ethyl acetate/toluene.

EXAMPLE 6

(A) (i) 2 g of racemic methyl 1,4,6,9-tetrahydro-6,9-dioxopyridazo[1,2-a]-pyridazine-1-carboxylate were dissolved in 50 ml of methanol and hydrogenated over 200 mg of 10% palladium-on-carbon for 2 hours at room temperature and atmospheric pressure. The catalyst was filtered off, the filtrate was evaporated and the residue was recrystallized from ethyl acetate to give 0.75 g (37%) of racemic methyl 1,2,3,4,6,9-hexahydro-6,9-dioxopyridazo[1,2-a]pyridazine-1-carboxylate in the form of a white solid of melting point 121° C.

(A) (ii) 1.20 g of racemic piperazic acid were dissolved in a mixture of 23 ml of water, 3 ml of concentrated hydrochloric acid and 1.5 ml of methanol. 0.90 g of maleic anhydride were added and the mixture was heated at reflux for 12 hours. After evaporation to dryness, the residue was dissolved in 40 ml of methanol previously saturated with hydrogen chloride. The solution was heated at reflux for 2.5 hours and then evaporated to give a brown oil. Chromatography on silica gel gave 0.63 g (30%) of racemic methyl 1,2,3,4,6,9-hexahydro-6,9-dioxopyridazo[1,2-a]pyridazine-1-carboxylate which, after recrystallization from chloroform/hexane, melted at 121.5° C.

(B) In a manner analogous to that described in Example 4(B), from 0.224 g of racemic methyl 1,2,3,4,6,9-hexahydro-6,9-dioxopyridazo[1,2-a]pyridazine-1-carboxylate there was obtained 0.04 g (13%) of racemic methyl 8-(acetylthio)methyl-octahydro-6,9-dioxopyridazo[1,2-a]pyridazine-1-carboxylate (diastereoisomer B) in the form of a white solid of melting point 128°–132° C. (from ethyl acetate/hexane).

EXAMPLE 7

(A) 49.5 g of racemic 1,4,6,9-tetrahydro-6,9-dioxopyridazo[1,2-a]pyridazine-1-carboxylic acid were suspended in 1 liter of boiling ethanol and a solution of 26.6 g of (+)-1-phenylethylamine in 200 ml of ethanol was added. After leaving to stand at 0° C., the crystalline salt was filtered off and recrystallized from ethanol to constant rotation, there being obtained 26.5 g of the (+)-1-phenylethylamine salt of the foregoing acid; $[\alpha]_{436}^{20} = +898°$ (c=0.5% in methanol). This salt was dissolved in 1 liter of 50% methanol and stirred with a sulphonic acid ion-exchange resin. The resin was filtered off and washed with 50% methanol. The filtrate and washings were combined and evaporated. The residue was crystallized from water to give 15.3 g of (+)-1,4,6,9-tetrahydro-6,9-dioxopyridazo[1,2-a]pyridazine-1-carboxylic acid hydrate; $[\alpha]_{436}^{20} = +1043°$ (c=0.5% in water).

In an analogous manner, using (−)-1-phenylethylamine there was obtained (−)-1,4,6,9-tetrahydro-6,9-dioxopyridazo[1,2-a]pyridazine-1-carboxylic acid hydrate; $[\alpha]_{436}^{20} = -1046°$ (c=0.5% in water).

(B) In a manner analogous to that described in Example 5(B), from (+)-1,4,6,9-tetrahydro-6,9-dioxopyridazo[1,2-a]pyridazine-1-carboxylic acid there was obtained (+)-methyl 8-(acetylthio)methyl-1,4,6,7,8,9-hexahydro-6,9-dioxopyridazo[1,2-a]pyridazine-1-carboxylate [melting point 114°–115° C; $[\alpha]_{436}^{20} = +1486°$ (c=0.5% in methanol)] and from (−)-1,4,6,9-tetrahydro-6,9-dioxopyridazo[1,2-a]pyridazine-1-carboxylic acid there was obtained (−)-methyl 8-acetylthio)methyl-1,4,6,7,8,9-hexahydro-6,9-dioxopyridazo[1,2-a]pyridazine-1-carboxylate [melting point 114°–115° C. $[\alpha]_{436}^{20} = -1438°$ (c=0.5% in methanol)].

(C) In a manner analogous to that described in Example 2, from 1.8 g of (−)-methyl 8-(acetylthio)methyl-1,4,6,7,8,9-hexahydro-6,9-dioxopyridazo[1,2-a]pyridazine-1-carboxylate there was obtained 0.46 g (48%) of (−)-8-(mercaptomethyl)-1,4,6,7,8,9-hexahydro-6,9-dioxopyridazo[1,2-a]pyridazine-1-carboxylic acid of melting point 139°–146° C. (decomposition) after recrystallization from ethyl acetate/toluene; $[\alpha]_{365}^{20} = -1779°$ (c=0.5% in methanol).

The following Examples illustrate pharmaceutical preparations containing the pyridazopyridazine derivatives provided by the present invention.

EXAMPLE A

Tablets containing the following ingredients are produced in a conventional manner:

| Ingredient | Per tablet |
| --- | --- |
| Pyridazopyridazine derivative | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients are produced in a conventional manner:

| Ingredient | Per capsule |
| --- | --- |
| Pyridazopyridazine derivative | 25.0 mg |
| Lactose | 150.0 mg |
| Maize starch | 20.0 mg |
| Talc | 5.0 mg |
| Total capsule content | 200.0 mg |

We claim:

1. Pyridazopyridazine compounds of the formula

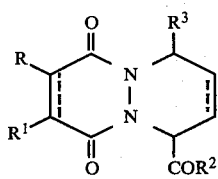

I wherein one of the symbols R and $R^1$ is hydrogen or lower alkyl and the other symbol is a group of the formula

   (i)

in which A is methylene, ethylene or propylene which may be substituted by lower alkyl, Y is mercapto, lower alkanoylthio, aroylthio or aryl-(lower alkylthio) and n is zero or 1, $R^2$ is hydroxy, lower alkoxy or amino, $R^3$ is hydrogen or lower alkyl or phenyl optionally substituted with halogen, lower alkyl, lower alkoxy or trifluoromethyl, and the broken lines denote optional bonds, and salts of the acids of formula I with pharmaceutically acceptable bases.

2. Pyridazopyridazine derivatives according to claim 1 wherein R is hydrogen, $R^1$ is a group of formula (i), $R^2$ is hydroxy or lower alkoxy, $R^3$ is hydrogen and a single-bond is present in the 7,8-position.

3. Pyridazopyridazine derivatives according to claim 2 wherein the group of formula (i) is mercaptomethyl or lower alkanoylthiomethyl.

4. Racemic methyl 8-acetylthio)methyl-octahydro-6,9-dioxopyridazo[1,2-a]pyridazine-1-carboxylate.

5. Racemic 8-(mercaptomethyl)-octahydro-6,9-dioxopyridazo[1,2-a]pyridazine-1-carboxylic acid.

6. A compound selected from the group consisting of racemic tert.butyl 8-(acetylthio)methyl-octahydro-6,9-dioxopyridazo[1,2-a]pyridazine-1-carboxylate, racemic 8-(acetylthio)methyl-octahydro-6,9-dioxopyridazo[1,2-a]-pyridazine-1-carboxylic acid, racemic methyl 8-(acetylthio)-methyl-1,4,6,7,8,9-hexahydro-6,9-dioxopyridazo[1,2-a]pyridazine-1-carboxylate, racemic 8-mercaptomethyl)-1,4,6,7,8,9-hexahydro-6,9-dioxopyridazo[1,2-a]pyridazine-1-carboxylic acid, (+)-methyl 8-(acetylthio)methyl-1,4,6,7,8,9-hexahydro-6,9-dioxopyridazo[1,2-a]pyridazine-1-carboxylate, (−)-methyl 8-(acetylthio)methyl-1,4,6,7,8,9-hexahydro-6,9-dioxopyridazo[1,2-a]-pyridazine-1-carboxylate and (−)-8-(mercaptomethyl)-1,4,6,7,8,9-hexahydro-6,9-dioxopyridazo[1,2-a]pyridazine-1-carboxylic acid.

7. A compound of formula

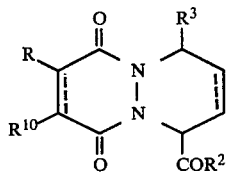

VII wherein one of the symbols R and $R^{10}$ is hydrogen or lower alkyl and the other symbol is a group of the formula

   (ii)

in which A is methylene, ethylene or propylene which may be substituted by lower alkyl, X is halogen and n is zero or 1, $R^2$ is hydroxy, lower alkoxy or amino, $R^3$ is hydrogen or lower alkyl or phenyl optionally substituted with halogen, lower alkyl, lower alkoxy or trifluoromethyl, and the broken lines denote optional bonds.

8. A compound of the formula

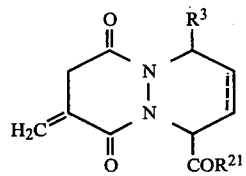

X wherein $R^3$ is hydrogen or lower alkyl or phenyl optionally substituted with halogen, lower alkyl, lower alkoxy or trifluoromethyl, $R^{21}$ is hydroxy or lower alkoxy, and the broken line denotes an optional bond.

9. A compound of the formula

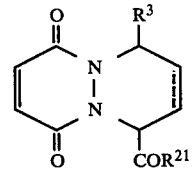

XVII wherein $R^3$ is hydrogen or lower alkyl or phenyl optionally substituted with halogen, lower alkyl, lower alkoxy or trifluoromethyl, $R^{21}$ is hydroxy or lower alkoxy, and the broken line denotes an optional bond.

10. An antihypertensive composition comprising antihypertensively-effective amounts of pyridazopyridazine compounds of the formula

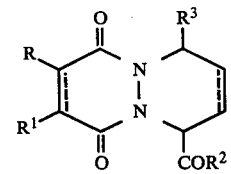

I wherein one of the symbols R and $R^1$ is hydrogen or lower alkyl and the other symbol is a group of the formula

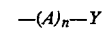   (i)

in which A is methylene, ethylene or propylene which may be substituted by lower alkyl, Y is mercapto, lower alkanoylthio, aroylthio or aryl-(lower alkylthio) and n is zero or 1, $R^2$ is hydroxy, lower alkoxy or amino, $R^3$ is hydrogen or lower alkyl or phenyl optionally substituted with halogen, lower alkyl, lower alkoxy or trifluoromethyl, and the broken lines denote optional bonds, and salts of the acids of formula I with pharmaceutically acceptable bases in combination with a pharmaceutically acceptable carrier material.

11. Antihypertensive compositions comprising pyridazopyridazine derivatives according to claim 10 wherein R is hydrogen, $R^1$ is a group of formula (i), $R^2$ is hydroxy or lower alkoxy, $R^3$ is hydrogen, and a single-bond is present in the 7,8-position in combination with a pharmaceutically acceptable carrier material.

12. Antihypertensive compositions comprising pyridazopyridine derivatives according to claim 11 wherein the group of formula (i) is mercaptomethyl or lower alkanoylthiomethyl in combination with a pharmaceutically acceptable carrier material.

13. Antihypertensive compositions comprising racemic methyl 8-acetylthio)methyloctahydro-6,9-dioxopyridazo[1,2-a]pyridazine-1-carboxylate in combination with a pharmaceutically acceptable carrier material.

14. Antihypertensive compositions comprising racemic 8-(mercaptomethyl)-octahydro-6,9-dioxopyridazo[1,2-a]-pyridazine-1-carboxylic acid in combination with a pharmaceutically acceptable carrier material.

15. Antihypertensive compositions comprising a compound selected from the group consisting of racemic tert.butyl 8-(acetylthio)methyl-octahydro-6,9-dioxopyridazo[1,2-a]pyridazine-1-carboxylate, racemic 8-(acetylthio)methyl-octahydro-6,9-dioxopyridazo[1,2-a]-pyridazine-1-carboxylic acid, racemic methyl 8-(acetylthio)-methyl-1,4,6,7,8,9-hexahydro-6,9-dioxopyridazo-[1,2-a]pyridazine-1-carboxylate, racemic 8-(mercaptomethyl)-1,4,6,7,8,9-hexahydro-6,9-dioxopyridazo[1,2-a]pyridazine-1-carboxylic acid, (+)-methyl 8-(acetylthio)methyl-1,4,6,7,8,9-hexahydro-6,9-dioxopyridazo[1,2-a]pyridazine-1-carboxylate, (−)-methyl 8-acetylthio)methyl-1,4,6,7,8,9-hexahydro-6,9-dioxopyridazo[1,2-a]-pyridazine-1-carboxylate and (−)-8-(mercaptomethyl)-1,4,6,7,8,9-hexahydro-6,9-dioxopyridazo [1,2-a]pyridazine-1-carboxylic acid in combination with a pharmaceutically acceptable carrier material.

* * * * *